US00PP08554P

United States Patent [19]

Bennett, deceased et al.

[11] Patent Number: Plant 8,554

[45] Date of Patent: Jan. 25, 1994

[54] MINIATURE ROSE PLANT NAMED 'HANKY PANKY'

[76] Inventors: Cecilia L. D. Bennett, deceased, late of Chula Vista, Calif., by Susan M. O'Brien, administrator; Susan M. O'Brien, 489 Minot Ave., Chula Vista, Calif. 91910

[21] Appl. No.: 999,368

[22] Filed: Dec. 31, 1992

[51] Int. Cl.[5] ..... A01H 5/00

[52] U.S. Cl. ..... Plt./10.1

[58] Field of Search ..... Plt. 7.1, 10.1

*Primary Examiner*—James R. Feyrer

[57] ABSTRACT

The subject of the present disclosure is a new and distinct variety of miniature rose plant, named 'Hanky Panky' which is characterized by buds ranging from near Carrot Red to near Chinese Coral and blooms ranging from near Orange Buff to near Chinese Coral. Blooms of this rose are usually borne one to a stem with hybrid tea form and in sprays of 3 to 5 or more. The bush is vigorous, well-branched and produces moderate to heavy blooms.

1 Drawing Sheet

The present invention relates to a new and distinct variety of a hardy, dwarf, bush plant of the miniature class; the variety being primarily characterized as orange and pink blend.

The variety is further characterized by:

Long stemmed blooms of hybrid tea-type form, borne usually one to a stem and in compact sprays of 3 to 5 or more. The blooms are held very erect and well above the foliage.

The plant ranges in height from 18 to 24 inches (45 to 60 cm). The canes are sturdy and erect with moderate branching and medium to heavy foliage covering. The plant is a heavy bloomer that does well either in the greenhouse or outdoors.

The plant has good growth habits, well-shaped and attractive, bearing numerous leaflets of average size. I have found this variety to be easily asexually reproduced from cuttings at the nursery located at 489 Minot Avenue, Chula Vista, Calif.

The seed parent was Deep Purple U.S. Plant Pat. No. 4,672 (Hybridised by Kordes; introduced by Armstrong Nurseries in 1980; Zorina U.S. Plant Pat. No. 2,321, × Silver Star, unpatented), and the pollen parent was Party Girl (U.S. Plant Pat. No. 4,598). It differs from its seed parent in the following ways. It is a miniature rose of the orange blend class, and Deep Purple is a floribunda of the mauve class. It differs from its pollen parent in the following ways. It produces blooms in shades of orange to coral, alone, or blended with or even predominated by pink, and Party Girl produces blooms in pale yellow with a blush of pink on the outer petals. The flowers of this plant are highly unusual among the those of plants within the market class in that they may be predominantly pink or predominantly orange, as a function of season and exposure to light. Buds formed and opening in warm weather tend to be more orange than those formed in cooler weather; while buds formed in sunny locations or in full sun tend to be more orange and less pink than those formed on plants which may receive direct sun for only part of the day. This plant may be accurately described as being more photo-sensitive and temperature sensitive in its flower pigmentation, when compared with other miniature roses of similar type, with regard to ultimate flower color. The flower color of this plant has also been observed to be more predominantly orange when budded to tree form, presumably due to enhanced exposure to light from all angles.

The single color photographic view shows, in plain view, a bouquet of 'Hanky Panky' in various stages of maturity from bud stage to nearly open bloom stage.

The descriptive matter which follows pertains to roses grown and color values observed in plants and newly opened blooms in the months of March through November of 1992. The plants were grown outdoors in Chula Vista, Calif., and are believed to be accurate standards for this cultivar in similar conditions of soil and climate elsewhere.

Referring now specifically to the new and distinct variety of miniature rose plant named 'Hanky Panky', the following is a detailed description thereof in outline; all major color plate identifications being by reference to the British Colour Council Horticultural Chart, except where common terms of color definition are employed.

Type: Hardy, dwarf, bushy, greenhouse or outdoor, exhibition or garden decorative potted plant.

Class: Miniature. It is anticipated that this plant will be classified as an orange and pink blend for purposes of color classification.

Variety name: Hanky Panky.

Flowers borne: Usually one to a stem, but occasionally in sprays of 3 to 5 or more on erect stems with foliage well below the blooms.

Quantity of bloom: Heavy both outdoors or greenhouse grown.

Bud:

*Peduncle.*—Average length (30 to 50 mm); average diameter and sturdy; ranging from near Scheeles Green (860/3 to 860/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Average for a miniature variety (40 to 50 mm).

*Petalage.*—Full — 25 to 35 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped. Blooms are of hybrid tea form.

Petals: Fairly thick with good substance; both the upper and under surfaces of all petals have a matte finish. Shape — Outer petals are of a broad obovate form. Outer petals may be slightly lobed, and normally contain a slight point in the margin between the lobes on essentially the center line of the petals; lobes softly reflex with maturity but petals remain slightly cupped. The intermediate petals are very much like the outer petals only narrower. The inner petals are a broad lanceolate form; and the petaloids are also lanceolate with some occasional irregularities.

Color: Newly opened flowers from plants grown outdoors (March through November of 1992), Chula Vista, Calif.

*All petals.*—Upper surfaces — Ranging from near Chinese Coral (614/3 to 614/1 page 72) to near Orange Buff (507/3 to 507 page 133) during warm weather and ranging from near Chinese Coral (614/3 to 614/1 page 72) to near Carrot Red (612/3 to 612/1 page 71) in cooler weather. The outer petals fade to paler shades of near Chinese Coral to near Orange Buff. Under Surfaces — Slightly lighter tones of upper surfaces.

*General color effect.*—Newly opened flowers — Pale orange to pale coral in warm weather; pale coral to nearly peach-pink in cooler weather. Three days open — Slight fading of outer petals. Flowers of this plant are characteristically variable in color due to seasonal temperature changes and exposure to sunlight. Generally, flowers grown in full sun tend to be more orange than pink and may even appear to be pure orange, especially when grown in warm weather. During cooler weather, and under less than full sun, flowers may be predominantly pink, but will normally express some coral or orange shades, particularly near the central portion of the flower. Three to five days open — Continued fading of all petals to softest tones of orange and coral.

*Flower longevity (March through November 1992).*—Plant in pot 5 to 7 days from bud with sepals reflexed to fully open bloom. Holding at fully opened for 5 to 7 days longer. Cut blooms at living room temperature 10 to 14 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow.

*Ovaries.*—All encased in calyx.

*Hips.*—Some.

*Seeds.*—3 to 5 or more in each hip.

*Sepals.*—Permanent; spear-shaped; open as the bloom opens, recurving against the peduncle, when the bloom is fully opened. Occasional foliaceous appendages attractively supplement sepal terminals; these are of varying lengths.

Foliage:

*Leaves.*—5 to 7 leaflets on average; medium size for a miniature rose plant.

*Leaflets.*—Broad ovate-shaped.

*Margins.*—Very serrated with tinting of bronze, especially noticeable on the newer foliage.

*Color.*—Ranging from near Spinach Green (0960/3 to 0960 page 187) to near Scheeles Green (860/1 to 860 page 175) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bush; above average for a miniature rose plant.

*Rate and character.*—Vigorous and well-branched.

*Canes.*—Medium diameter; sturdy; held erect.

*Main stems.*—Color range same as foliage.

*Thorns.*—Averaging less than 5 to 10 per 10 cm on the main stems and branches. Reddish in color; average size; slender and hooked slightly downward.

*Branches.*—Coloration ranges the same as does that of the foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant, named 'Hanky Panky', hardy, dwarf, vigorous growth, well-branched and attractive in appearance, substantially as illustrated and described; characterized by its hybrid tea form blooms, ranging from near Chinese Coral to near Orange Buff to near Carrot Red that pales in tones as the blooms open, the blooms are abundant on the bush and usually borne one to a stem but occasionally in sprays of 3 to 5 or more.

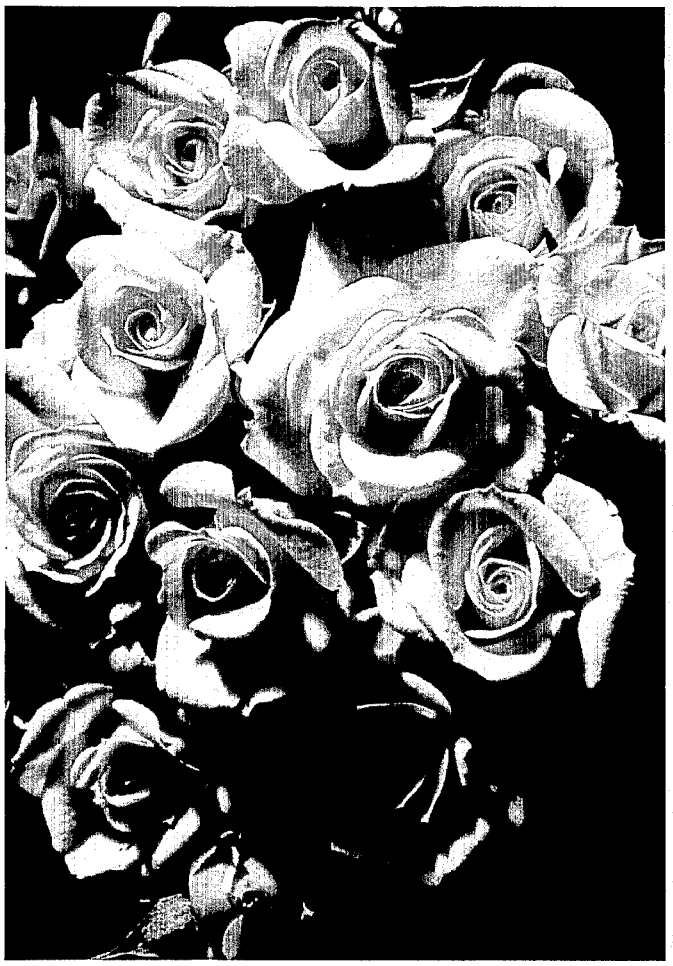

* * * * *